United States Patent [19]

Arnold et al.

[11] 4,151,358

[45] Apr. 24, 1979

[54] ETHYNYL-SUBSTITUTED BIS-NAPHTHALIMIDES

[75] Inventors: Fred E. Arnold, Centerville; Frederick L. Hedberg, Dayton, both of Ohio

[73] Assignee: The United States of America as represented by the Secretary of the Air Force, Washington, D.C.

[21] Appl. No.: 870,793

[22] Filed: Jan. 19, 1978

Related U.S. Application Data

[62] Division of Ser. No. 750,945, Dec. 15, 1976, Pat. No. 4,086,248.

[51] Int. Cl.$^2$ .................. C07D 401/12; C07D 401/10

[52] U.S. Cl. ...................................................... 546/98
[58] Field of Search ................................ 260/281 NH

[56] References Cited

U.S. PATENT DOCUMENTS 3,402,166  9/1968  Heckl ........................... 260/281 NH Primary Examiner—Mark L. Berch
Attorney, Agent, or Firm—Joseph E. Rusz; Cedric H. Kuhn

[57] ABSTRACT

As new compositions of matter, ethynyl-substituted aromatic 'peri' anhydrides. The compounds are useful as endcapping agents for thermally stable heterocyclic imide compositions.

6 Claims, No Drawings

ETHYNYL-SUBSTITUTED BIS-NAPHTHALIMIDES

RIGHTS OF THE GOVERNMENT

This is a division, of application Ser. No. 750,945, filed Dec. 15, 1976, and issued on Apr. 25, 1978, as U.S. Pat. No. 4,086,248.

The invention described herein may be manufactured and used by or for the Government of the United States for all governmental purposes without the payment of any royalty.

FIELD OF THE INVENTION

This invention relates to ethynyl-substituted aromatic 'peri' anhydrides. In one aspect it relates to a method for synthesizing the compounds. In another aspect it relates to bis-ethynyl imide compositions containing six-membered rings.

BACKGROUND OF THE INVENTION

One of the most promising classes of candidate materials for high temperature composite and adhesive applications has been the aromatic imide compositions. In particular, the six-membered imide system has demonstrated excellent thermooxidative properties and resistance to hydrolysis from environmental moisture.

Unfortunately, the imide systems are formed by condensation reactions with the evolution of volatile by-products. In the fabrication of reinforced composite structures, the volatile by-products, which are evolved, form voids which greatly weaken the structures. There is a real need, therefore, for an imide composition which possesses all the required fabrication criteria while having the capability of being converted to a thermally stable, high molecular weight polymer by a non-volatile addition reaction. Furthermore, the most attractive six-membered imide system has not been utilized as a composite or adhesive material because of its inability to form a high molecular weight polymer by the normal condensation process.

It is a principal object of this invention, therefore, to provide ethynyl-substituted aromatic 'peri' anhydrides which can be used as endcapping agents in the synthesis of imide compositions, thereby enabling such systems to cure by addition reactions.

Another object of the invention is to provide new and improved bis-ethynyl 'peri'imide compositions which polymerize via addition reactions.

A further object of the invention is to provide a method for synthesizing the endcapping agents.

Other objects and advantages of the invention will become apparent to those skilled in the art upon consideration of the accompanying disclosure.

SUMMARY OF THE INVENTION

The present invention resides in an ethynyl-substituted aromatic 'peri' anhydride having the following formula:

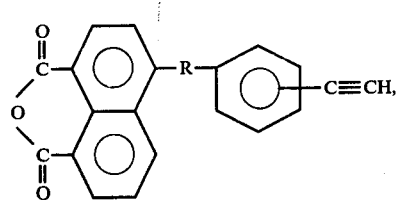

wherein R is oxygen or sulfur and the ethynyl group is ortho, meta, or para to R.

The 'peri' anhydrides of this invention are prepared by the nucleophilic displacement reaction of a nitro or halo leaving group of a naphthalic anhydride (IV) with a metallic salt of an ethynyl-substituted phenol or thiophenol (III). The metallic salt is generated from the base hydrolysis of the corresponding tosylated phenol or thiophenol (II). The reactions involved are shown by the following equations:

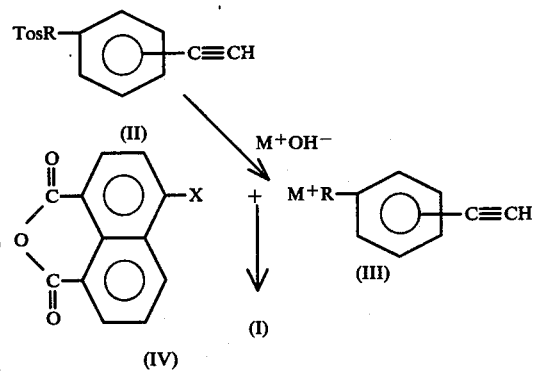

In the foregoing equations, Tos is CH$_3$

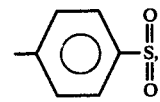

R is oxygen or sulfur, M is an alkali metal, such as potassium or sodium, and X (leaving group) is nitro, fluorine, chlorine, iodine or bromine.

The compounds of this invention are especially useful for synthesizing bis-ethynyl 'peri' imide compositions which cure by non-volatile addition reactions. There is thus provided high molecular weight, moisture insensitive matrix and adhesive resins which have previously been unattainable by a condensation process. The bis-ethynyl 'peri' imide compositions are prepared by the reaction of two moles of the endcapping agent with one mole of an aromatic diamine. The reaction involved can be represented by the following equation:

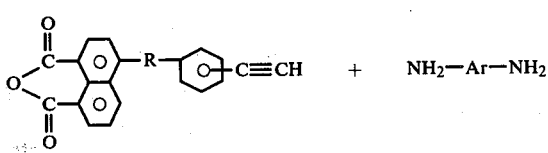

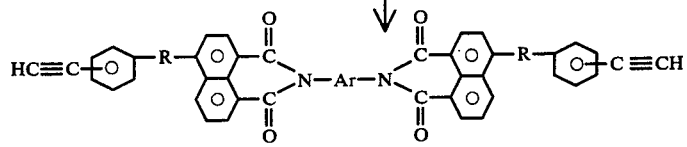

In the foregoing equation, R is oxygen or sulfur and Ar is a divalent aromatic radical.

Examples of divalent aromatic radicals (Ar) include the following:

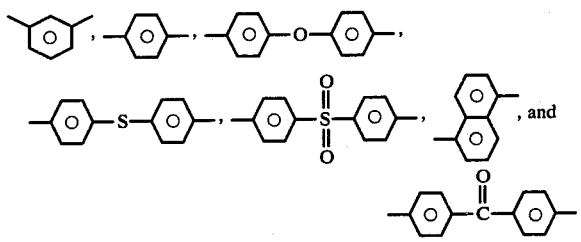

A more complete understanding of the invention can be obtained by referring to the following illustrative examples which are not intended, however, to be unduly limitative of the invention.

EXAMPLE I 4-(3-ethynylphenoxy)naphthalic anhydride from 4-nitronaphthalic anhydride To 100 ml of anhydrous methanol was added 20 g (0.073 mole) of 3-ethynylphenyl(p-toluenesulfonate) and 8.19 g (0.146 mole) of potassium hydroxide. The mixture was heated to reflux, under a nitrogen atmosphere and maintained at reflux for four hours. A distillation apparatus was attached to the flask, and methanol was distilled from the flask until the residue approached dryness. Then, 400 ml of anhydrous benzene was added, and distillation continued until 200 ml of benzene was removed. The reaction mixture was freeze-dried under high vacuum, leaving a dry, white powder. To the freeze-dried material was added a solution containing 12.1 g (0.05 mole) of 4-nitronaphthalic anhydride dissolved in 300 ml of anhydrous N,N-dimethylacetamide (DMAC). The mixture was heated to 100° C., under a nitrogen atmosphere, and maintained at that temperature for 12 hours. The reaction mixture was allowed to cool to room temperature and poured into diethylether to precipitate the inorganic salts which were removed by filtration. The diethylether/DMAC solvent was removed in vacuo at 90° C., by means of a rotary evaporator leaving a residual oil. The oil was dissolved in methylene chloride and filtered through a 2"×6" dry column of silica gel while eluting the column with methylene chloride. The eluate was evaporated to dryness, yielding 12.5 g (80%) of 4-(3-ethynylphenoxy)-naphthalic anhydride.

Analysis Calc'd for $C_{20}H_{10}O_4$: C, 76.42; H, 3.20
Found: C, 75.96; H, 2.82

EXAMPLE II 4-(3-ethynylphenoxy)naphthalic anhydride from 4-bromonaphthalic anhydride To 100 ml of anhydrous methanol was added 20 g (0.073 mole) of 3-ethynylphenyl(p-toluenesulfonate) and 8.19 g (0.146 mole) of potassium hydroxide. The mixture was heated to reflux, under a nitrogen atmosphere and maintained at reflux for four hours. The methanol solvent was removed in vacuo at 40° C. by means of a rotary evaporator, leaving a dry, white powder. The white powder was dissolved in 100 ml of dimethylsulfoxide (DMSO) and added dropwise to a DMSO solution containing 13.8 g (0.05 mole) of 4-bromonaphthalic anhydride at 90° C. The mixture was heated at 100° C., under a nitrogen atmosphere, for 12 hours. The reaction mixture was allowed to cool to room temperature and poured into diethylether to precipitate the inorganic salts which were removed by filtration. The diethylether/DMSO solvent was removed in vacuo at 90° C., by means of a rotary evaporator leaving a residual oil. The oil was dissolved in methylene chloride and filtered through a 2""×6" dry column of silica gel while eluting the column with methylene chloride. The eluate was evaporated to dryness, yielding 7.8 g (50%) of 4-(3-ethynylphenoxy)naphthalic anhydride.

Analysis Calc'd for $C_{20}H_{10}O_4$: C, 76.42; H, 3.20
Found: C, 76.23; H, 3.65

EXAMPLE III

Condensation of the anhydride of Example I with m-phenylenediamine:

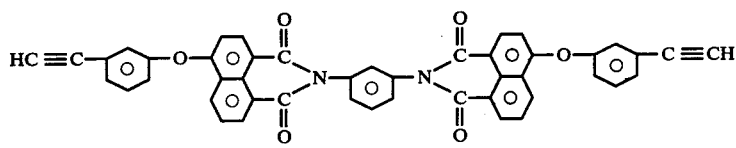

To a m-cresol solution containing 1 g (0.01 mole) of m-phenylenediamine was added 6.28 g (0.02 mole) of 4-(3-ethynylphenoxy)naphthalic anhydride. The mixture was heated to the reflux temperature of the solvent under a nitrogen atmosphere and maintained at that temperature for four hours. The reaction mixture was allowed to cool to room temperature and poured into anhydrous methanol to precipitate a light yellow material. The material was then dissolved in tetrahydrofuran and precipitated into diethylether to give a 6.5 g (95%) yield. The bis ethynyl imide composition softened at 195° C. and exhibited a polymerization maximum of 275° C. as evidenced from differential scanning calorimetry (DSC) at a heating rate of 20° C./min.

Analysis Calc'd for $C_{46}H_{25}O_6N_2$: C, 79.95; H, 3.64
Found: C, 79.21; H, 3.20

EXAMPLE IV

Condensation of the anhydride of Example I with oxydianiline:

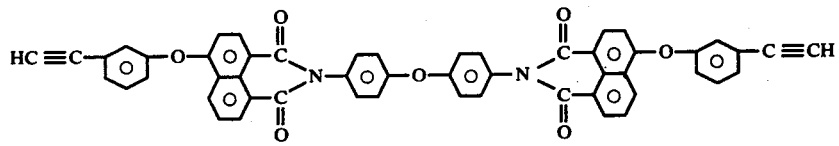

To a solution containing 2 g (0.01 mole) of oxydianiline dissolved in fresh distilled m-cresol was added 6.28 g (0.02 mole) of 4-(3-ethynylphenoxy)naphthalic anhydride. The mixture was heated to reflux under a nitrogen atmosphere and maintained at that temperature for four hours. The reaction mixture was allowed to cool to room temperature and poured into a 50% methanol/water mixture to precipitate a light yellow material. The material was dissolved in tetrahydrofuran and precipitated into water to give a 7.3 g (98%) yield. Analysis of the imide by DSC (heating rate of 20° C./min) showed a softening point of 185° C. and a strong exotherm maxi-mixing at 275° C. for the polymerization of the bis ethynyl groups.

Analysis Calc'd for $C_{48}H_{28}O_7N_2$: C, 77.40; H, 3.78
Found: C, 76.30; H, 3.95

The data in the foregoing examples demonstrate that the ethynyl-substituted aromatic 'peri' anhydrides of this invention can be used in preparing bis-ethynyl imide compositions. The data also show that the imide compositions have a softening point below their cure temperature, a characteristic which renders them eminently suitable for use in fabricating composites. Furthermore, during the curing process, no by-products are evolved, thereby eliminating the presence of voids which are found in prior art polyimides.

As will be evident to those skilled in the art, modifications of the present invention can be made in view of the foregoing disclosure without departing from the spirit and scope of the invention.

We claim:

1. A bis-ethynyl 'peri' imide having the following formula:

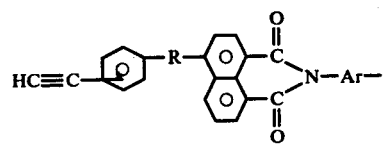

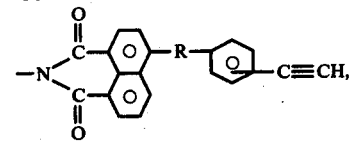

where R is oxygen or sulfur and Ar is

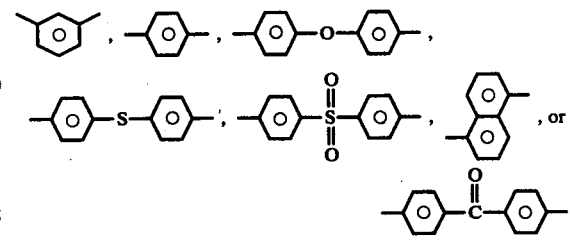

2. The imide according to claim 1 in which Ar is

3. The imide according to claim 1 in which Ar is

4. The imide according to claim 1 in which Ar is

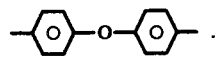

5. The imide according to claim 1 in which Ar is

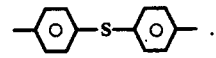

6. The imide according to claim 1 in which Ar is

* * * * *